(12) United States Patent
Katerkamp et al.

(10) Patent No.: US 8,551,059 B2
(45) Date of Patent: Oct. 8, 2013

(54) SPINAL CANNULA HAVING LIQUOR DETECTION

(75) Inventors: Andreas Katerkamp, Melsungen (DE); Volker Schumacher, Bad Waldsee (DE); Robert Klug, Eichstetten (DE); Martin Sippel, Melsungen (DE)

(73) Assignee: B. Braun Melsungen AG, Melsungen (DE)

( * ) Notice: Subject to any disclaimer, the term of this patent is extended or adjusted under 35 U.S.C. 154(b) by 136 days.

(21) Appl. No.: 12/936,570

(22) PCT Filed: Apr. 8, 2009

(86) PCT No.: PCT/EP2009/002615
§ 371 (c)(1), (2), (4) Date: Dec. 3, 2010

(87) PCT Pub. No.: WO2009/124751
PCT Pub. Date: Oct. 15, 2009

(65) Prior Publication Data
US 2011/0071480 A1    Mar. 24, 2011

(30) Foreign Application Priority Data
Apr. 8, 2008 (DE) .......... 10 2008 017 807

(51) Int. Cl.
*A61M 5/32* (2006.01)

(52) U.S. Cl.
USPC .............. 604/272; 604/168.01; 604/533

(58) Field of Classification Search
USPC ................ 604/168.01, 272, 533
See application file for complete search history.

(56) References Cited

U.S. PATENT DOCUMENTS

| 5,030,207 | A | 7/1991 | Mersch et al. |
| 5,496,281 | A | 3/1996 | Krebs |
| 6,656,161 | B2 | 12/2003 | Young et al. |
| 2002/0055715 | A1 | 5/2002 | Young |
| 2006/0116660 | A1 | 6/2006 | Cawley |
| 2008/0065017 | A1* | 3/2008 | Racz et al. .......... 604/158 |

FOREIGN PATENT DOCUMENTS

| DE | 200 01 205 | 3/2000 |
| EP | 0 522 737 | 1/1993 |
| EP | 0 682 954 | 11/1995 |

OTHER PUBLICATIONS

International Search Report for PCT/EP2009/002615 dated Aug. 27, 2009.

* cited by examiner

*Primary Examiner* — Emily Schmidt
(74) *Attorney, Agent, or Firm* — RatnerPrestia

(57) ABSTRACT

A spinal cannula with a needle hub having a transparent area for observing the liquor flowing through a hollow cavity of the needle hub. A structure for refracting or reflecting rays of light is provided in or at the transparent area of the needle hub. The structure for refracting or reflecting rays of light may be formed as one or more prisms.

12 Claims, 8 Drawing Sheets

SPINAL CANNULA HAVING LIQUOR DETECTION

CROSS REFERENCE TO RELATED APPLICATIONS

This application is the U.S. national phase application of PCT International Application No. PCT/EP2009/002615, filed Apr. 8, 2009, which claims priority to German Patent Application No. DE 10 2008 017 807.1, filed Apr. 8, 2008, the contents of such application being incorporated herein by reference.

FIELD OF THE INVENTION

The invention relates to a spinal cannula with a needle hub having a transparent area for observing the spinal fluid (liquor or cerebrospinal fluid CSF) flowing through the needle hub.

BACKGROUND OF THE INVENTION

Spinal cannulas are used for puncturing the spinal cavity, wherein the liquor backflow must be controlled so that the correct positioning of the needle tip in the subarachnoid cavity can be controlled. The difficulty hereby is that the water-white and colourless liquor cannot easily be optically recognised in the needle hub.

From U.S. Pat. No. 6,656,161, a spinal cannula having a transparent area at the needle hub is known, at which a magnifying lens is formed so that the liquor backflow can be recognised.

From EP 682 954, a spinal cannula having a transparent grip part is known, in which a liquor control chamber tapering toward the needle end is formed, which has a substantially rectangular cross-sectional shape with flat wall areas extending toward each other pair-wise in a wedge-shaped manner. In this embodiment, it is to be ensured that the liquor backflow inside the liquor control chamber is well recognisable without interfering reflexes and light refraction.

SUMMARY OF THE INVENTION

The invention relates to the object of forming a spinal cannula of the type mentioned above such that the liquor backflow can be better optically controlled.

A means for refracting or reflecting rays of light, for example a roof prism or triple prism, is provided at, on or in the transparent area of the needle hub. As long as no liquor backflow is taking place and only air is present in the needle hub, a different optical image is displayed to the user by the means for refracting or reflecting rays of light, than is displayed for liquor backflow when liquor is in the needle hub, wherein the liquor changes the refraction or reflection of the rays of light and thereby a different optimal image results. In this way, it can be determined very clearly whether liquor backflow is taking place or not.

When the means for reflecting rays of light is formed as a prism, simple design alternatives of the spinal cannula result, wherein the prism can be formed on the outer circumference of the needle hub or of the transparent area or on the inner circumference of an observation chamber in the needle hub.

For improving recognition, the outer prism, seen in the direction of viewing, can be associated with least one bent area of the hollow cavity or of the outer circumference of the needle hub as a means for refracting rays of light.

According to a further embodiment, rows of outer prisms can be formed offset to each other in the axial direction along the circumference, wherein the prisms in each row are at a distance from each other in the circumferential direction. In this way, a change in the refraction or reflection of the rays of light results in the area of a plurality of prisms, when liquor is in the observation area.

This effect is also achieved when a plurality of inner prisms are formed adjacent each other on the inner circumference of the observation chamber in the needle hub.

According to another embodiment, at least one prism area can delimit the hollow cavity or the observation chamber in the needle hub, to achieve a change in the optical image when liquor reaches the observation chamber.

Advantageously, the prism or the prisms can be moulded on at the spinal cannula, to make manufacturing cost-effective.

To improve the light refraction or light reflection, the means for reflecting rays of light can be formed as a reflective layer which is applied at the outer circumference in the transparent area of the needle hub, wherein the reflective side faces the hollow cavity.

The handling of the spinal cannula is facilitated in that the spinal cannula is surrounded by a grip collar having at least one recess on the circumference which grip collar is arranged over the means for refracting or reflecting rays of light.

The embodiment according to aspects of the invention can also be provided at another hollow body, especially at a flexible tube having at least one transparent wall portion, wherein a means for refracting or reflecting rays of light is provided in the area of the transparent wall portion, for optical recognition of fluid in the hollow cavity or flexible tube. Hereby, the means for refracting or reflecting rays of light can be formed in shapes described in connection with spinal cannulas.

The invention also comprises combinations of single or plural features described above. For example, an inner and an outer prism can be provided in the observation area, and a prism or a plurality of prisms can be used in connection with a reflective layer. By combining the described embodiments, the recognition of liquor can be improved.

BRIEF DESCRIPTION OF THE DRAWINGS

Exemplary embodiments of the invention are explained in more detail below with reference to the drawing, in which FIG. 1 schematically shows a spinal cannula with, for example, a round cross-section of the needle hub, FIG. 2 schematically shows a cross-section of a spinal cannula with a prism in the inner area, FIG. 3 schematically shows a cross-section of a spinal cannula with a prism in the outer area.

DETAILED DESCRIPTION OF THE INVENTION

Figure 1:
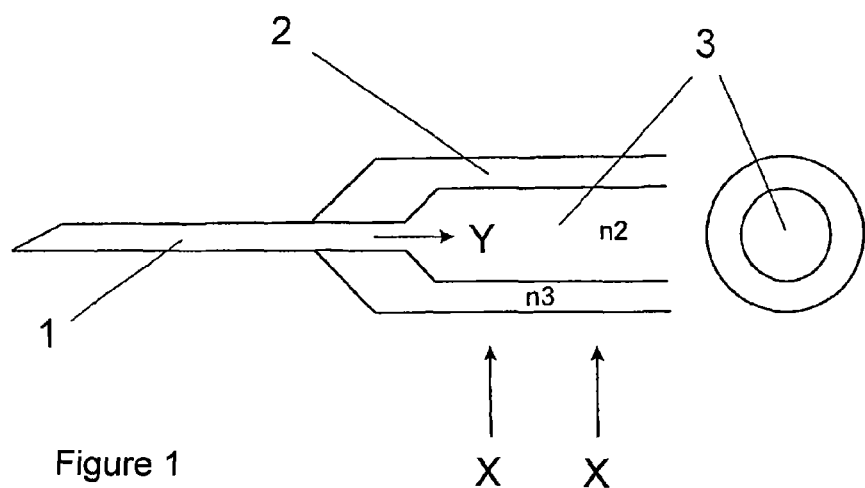

FIG. 1 shows a spinal cannula in a schematic longitudinal section, having a needle 1 fixed in a needle hub 2. The needle hub 2 has at least one transparent area or a viewing window having a refractive index n3, through which the hollow cavity 3 having a refractive index n2 (air) in the catheter hub can be observed. This hollow cavity 3 forms an observation chamber. Optical or visual observation takes place in the Figures in the direction of the arrows X. The entry of the liquor into the hollow cavity 3 takes place in the Figures via the needle 1 in the direction of the arrow Y.

Figure 2:
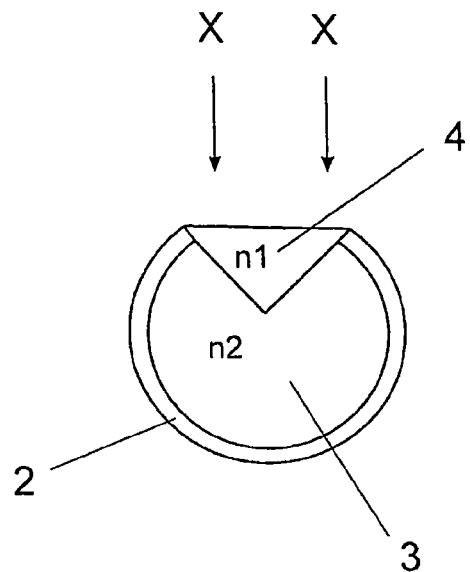

FIG. 2 shows an embodiment in which a prism 4 having a refractive index n1 is attached in the area of the viewing window such that the prism 4, called inner prism in the text below, extends inwards into the hollow cavity 3 by means of the two gable-shaped areas. In this embodiment, the needle hub 2 has a round or hollow cylindrical cross-sectional shape, wherein the inner prism 4 is integrated into the cross-section of the needle hub such that the basal plane of the prism forms a bevel on the outer circumference of the needle hub 2. As long as air is present in the observation chamber 3 of the needle hub 2, a clearly recognisable metallic luster is perceived in the area of the inner prism by viewing through the prism 4 along the arrows X. As soon as the air in the observation chamber 3 is displaced by the liquor, this metallic luster disappears and the area appears transparent.

In the embodiment shown schematically in FIG. 3, the prism 4' having a refractive index n1 is arranged such that the two gable-shaped areas face outwards and the basal plane of the prism, called outer prism below, forms a bevel on the inner circumference of the hollow cavity 3. In this way, a different image results, which is observed through a viewing window along the arrows X, which viewing window is formed diametrically opposite the prism 4'. As long as air is present in the observation chamber 3, only a hardly perceptible, small patch having metallic luster is recognisable in the area of the prism 4'. This shining reflex becomes larger and occurs clearly only when liquor displaces the air in the observation chamber 3.

Figure 4:
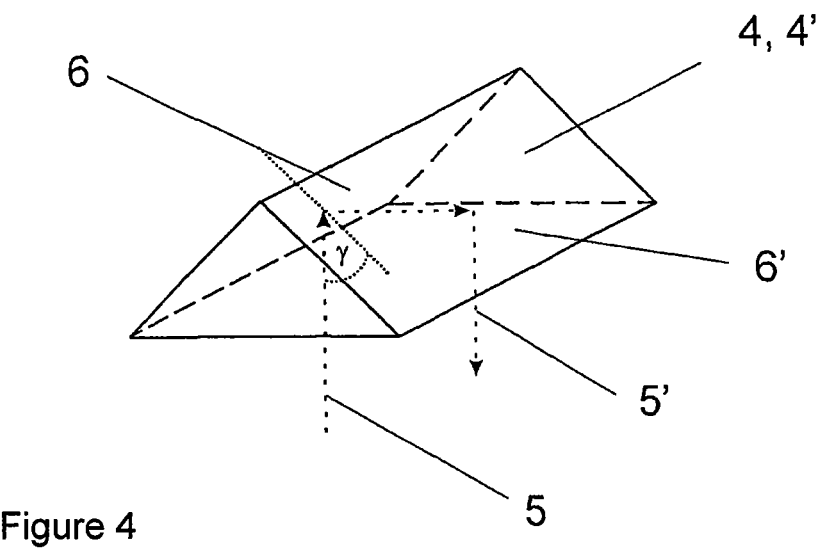
FIG. 4 shows a roof prism with incident, reflecting and emergent rays of light.

FIG. 4 shows a right-angled equal-sided prism, called roof prism below, which can be used as an inner prism 4 or outer prism 4'. The refractive index n1 of this prism can be, for example, between 1.42 and 1.62, and the refractive index n2 of the prism surroundings can be circa 1 when the prism is surrounded by air. Under these circumstances, an incident ray of light 5 experiences total reflection at the prism areas 6 and 6' when this ray of light falls onto the prism areas 6 and 6' at an angle γ of 45°. The emergent ray of light 5' is thus reflected or rotated by 180° in relation to the incident ray of light 5. Under these circumstances, an observer looking in the direction of the incident ray of light will perceive a light reflex. The conditions for total reflection at γ=45° are cancelled when the refractive index n2 of ca. 1 changes to larger than 1.32. This is the case for liquor at the prism areas. An observer looking in the direction of the incident ray of light 5 under these circumstances, cannot perceive any light reflex.

Figure 5:
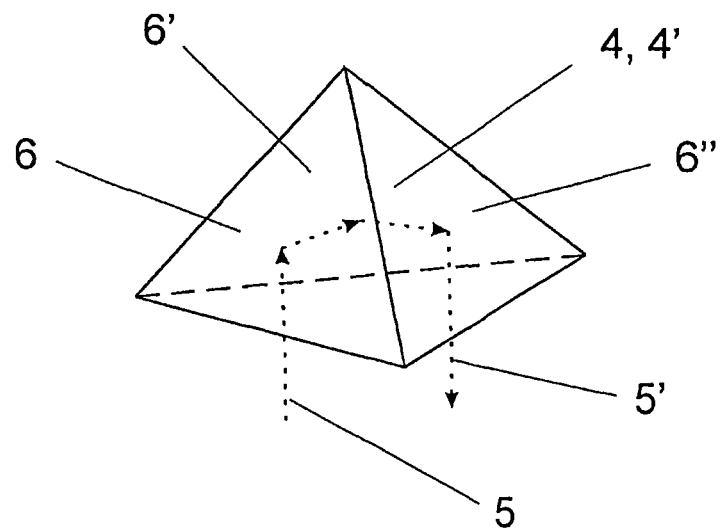
FIG. 5 shows a triple prism with incident, reflecting and emergent rays of light, FIG. 6 schematically shows a longitudinal section of a spinal cannula with a plurality of roof prisms in the inner area arranged adjacent each other on a circle, FIG. 7 schematically shows a longitudinal section of a spinal cannula with two opposing offset triple prisms in the outer area, FIG. 8 schematically shows a longitudinal section of a spinal cannula with a plurality of roof prisms in the inner area and a grip area with a perforated viewing window, FIG. 9 schematically shows a cross-sectional view of a spinal cannula with a reflective layer in the outer area instead of an outer prism, and FIG. 10 schematically shows a longitudinal view of a spinal cannula with two opposing offset reflective layers in the outer area instead of outer prisms.

FIG. 5 shows a triple prism which can be used as an inner prism 4 or outer prism 4'. Here, the same conditions apply again as for the roof prism in FIG. 4, with the difference that total reflection does or does not occur at three positions, according to the refractive index n2 of the triple prism surroundings at the three areas 6, 6' and 6".

Figure 6:
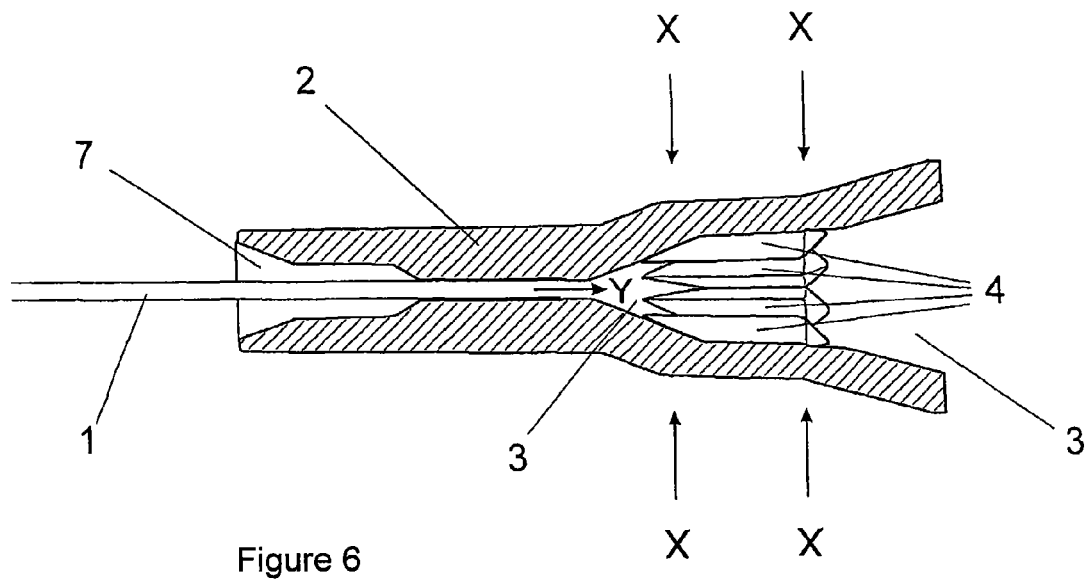

FIG. 6 shows a schematic longitudinal section of a spinal cannula having a transparent plastic needle hub 2 having a refractive index n3, in which the needle 1 is fixed at the needle hub through a clearance 7 filled with adhesive, and in which a plurality of inner prisms 4, formed by roof prisms with front areas each having a flattened tip, are arranged in a circular-symmetric manner on the inner circumference in the area of the viewing window. The roof prisms 4 consist of the same plastic material having a refractive index n1 as the needle hub 2 (n1=n3). This arrangement allows recognition of the liquor backflow from all sides for a viewing direction vertical to the longitudinal axis of the spinal cannula.

Figure 7:
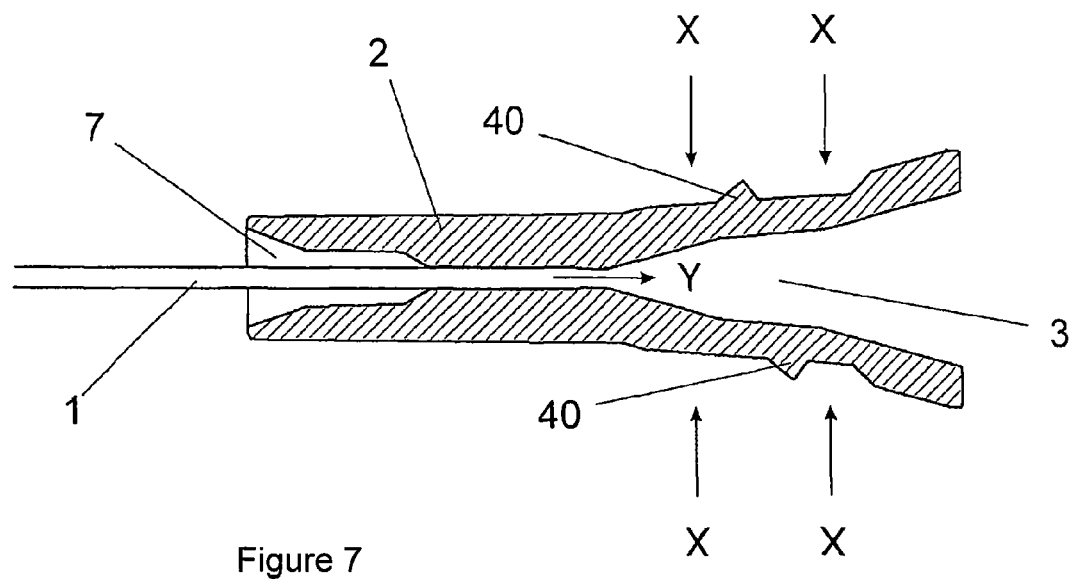

FIG. 7 shows a schematic longitudinal section of a spinal cannula having a transparent plastic needle hub 2 having a refractive index n3, in which the needle 1 is fixed at the needle hub through a clearance 7 filled with adhesive, and in which the outer prism is constructed of two rows 40 of triple prisms (FIG. 5) offset to one another and arranged behind each other vertical to the plane of the drawing. The triple prisms consist of the same plastic material with a refractive index n1 as the needle hub 2 (n1=n3). Instead of triple prisms, roof prisms (FIG. 4) can also be used in this arrangement. The single prisms of a row are preferably at such a distance from each other that, when viewing along the arrows X, the prism of the same row or of the other row, which prism is arranged on the opposite side, can be seen through this space or through the gap.

Figure 8:
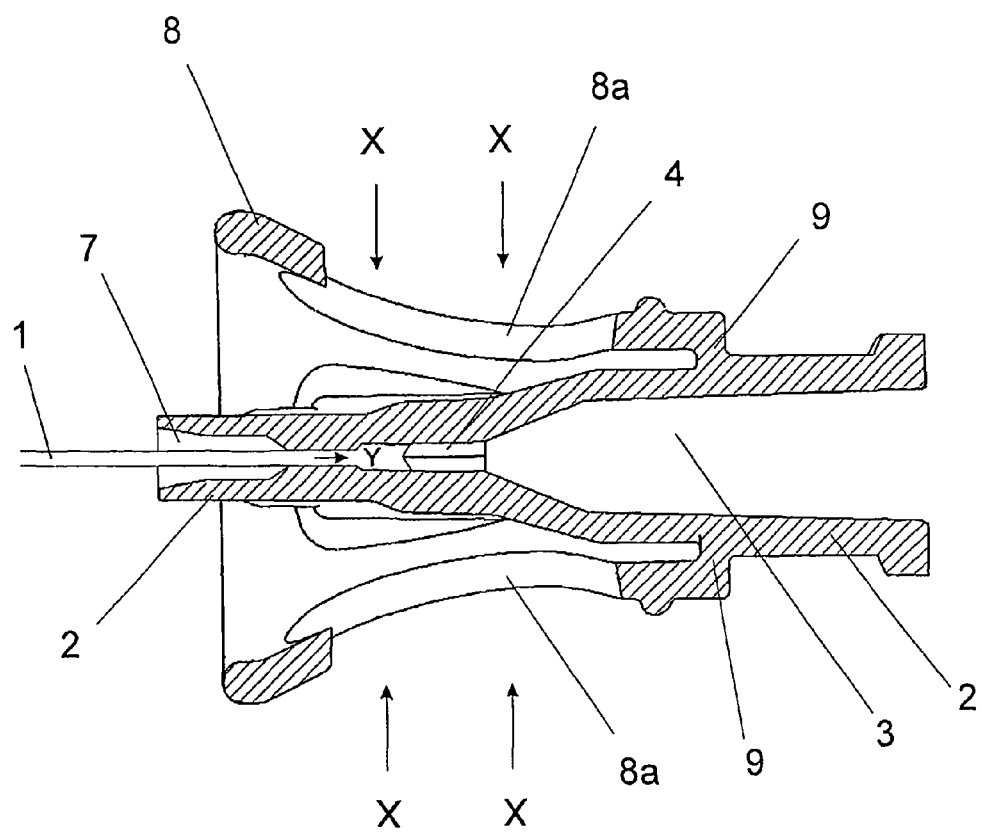

FIG. 8 shows a schematic longitudinal section of a spinal cannula similar to FIG. 6, wherein the needle hub 2 is additionally provided with a holding device 8 for improving the surface feel of the spinal cannula. This holding device is formed as a conical grip collar 8 around the needle hub 2 and is connected at the narrower end at 9 with the needle hub. The grip collar 8 has recesses 8a in the area of the viewing window of the needle hub 2, so that in the direction of the arrows X the liquor backflow can be determined by means of the inner prism 4 which lies opposite the recess 8a. The recesses 8a direct the eye of the observer to the viewing window therebelow with the prism. When for example four recesses 8a are provided on the circumference of the grip collar 8, on the inner circumference of the needle hub four prisms 4 are formed opposite the recesses 8a. Such a grip collar 8 can be moulded onto the spinal cannula or attached as a separate element and fixed for example by bonding.

Figure 9:
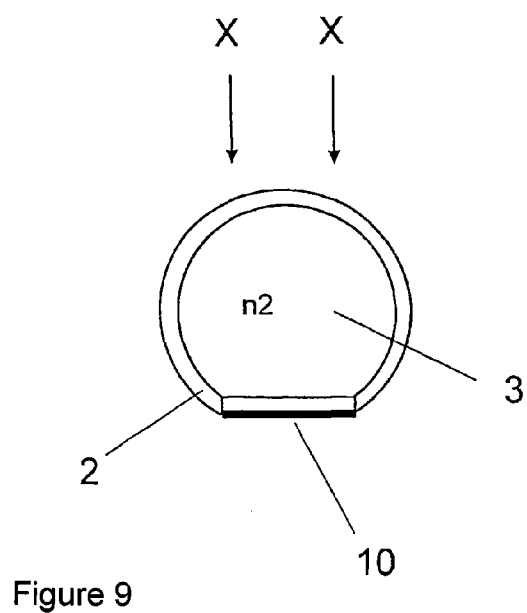

FIG. 9 shows another embodiment according to the invention in which instead of an outer prism a reflective layer 10, for example of silver or aluminium, is applied. Instead of such a reflective layer 10, an optical reflection grating can also be provided.

Figure 10:
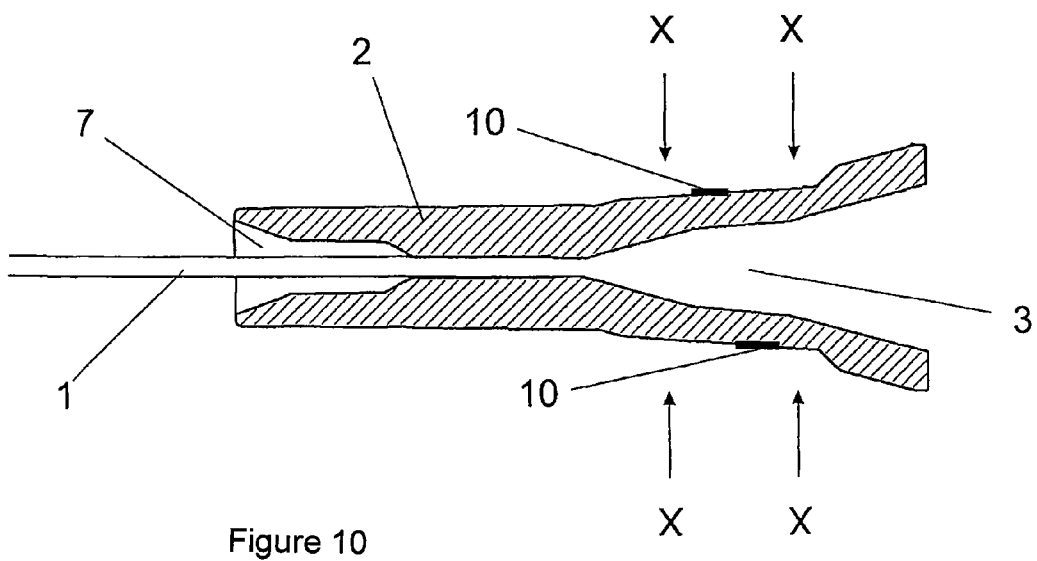

FIG. 10 shows a longitudinal section through a needle hub, wherein corresponding to FIG. 7 two rows of reflective layers 10 are applied on the outer circumference offset in the axial direction with a corresponding distance between the areas.

Through the change in the metallic luster in the direction of observation X in the viewing window, for all the embodiments according to FIGS. 2 and 3 and FIGS. 6, 7 and 8, the presence of the otherwise hardly recognisable transparent liquor in the hollow cavity 3 of the needle hub 2 can be clearly determined. This optical effect is achieved by the change in the refractive index of ca. 1 for air in the hollow cavity 3 to 1.32 to 1.35 for liquor in the hollow cavity 3.

For an inner prism 4 in the shape of a roof prism or triple prism, when air is present in the hollow cavity 3 a clear metallic luster is perceived in the area of the inner prism 4. This is achieved by the effect of total reflection as in FIGS. 4 and 5 with air as the prism surroundings. The incident angle γ, as of which total reflection occurs, is determined by γ=arcsin (n2/n1), wherein n2 is the refractive index of the prism surroundings in the hollow cavity 3 (water or liquor) and n1 is the refractive index of the prism 4, 4'. All the rays of light which fall on the side areas of the prism in FIG. 4 or 5 at a larger angle γ are subject to the effect of total reflection and are reflected at the side area 6 of the prism. As a total reflection occurs twice in the case of a roof prism and three times in the case of the triple prism, an angle of contingence γ of ca. 45° is preferably selected, because only in this way does an inversion or reflection of the ray of light occur through the prism 4, 4' by means of total reflection.

For a prism made of a common transparent plastic, the refractive index is between 1.42 and 1.6. The refractive index of air is ca. 1 and that of the liquor between 1.32 and 1.35. For air in the hollow cavity 3, an angle γ between 44.7° and 38.1° results; the angle γ should preferably be selected small to allow the largest possible area for the total reflection. Transparent plastics which fulfil these conditions with a refractive index of ca. 1.59 are polycarbonates (PC); however, other transparent polymers such as PMMA, CMMA, COC, SAN, PS and ABS are also suitable. For a prism made from PC, for air γ>38.9° applies and for liquor γ>56.1° to 58.1° applies. As an inversion of rays of light or reflection in a roof prism and triple prism only occurs at an angle of 45°, this condition is fulfilled for air in the hollow cavity 3, and it is not fulfilled for liquor in the hollow cavity 3. For an observer looking at the prism 4 preferably almost parallel to the incident ray of light in the direction of the arrows X according to FIGS. 2, 6 and 8, in the case of air in the hollow cavity a metallic luster is displayed by means of the reflection of the ray of light, and in the case of liquor in the hollow cavity 3, this reflection does not occur and the area appears transparent.

In an outer prism 4' in the shape of a triple prism, when air is present in the hollow cavity 3, a hardly perceptible small patch having metallic luster is perceived in the area of the outer prism. This is achieved by total reflection at the side areas 6, 6' and 6" of the triple prism, as shown in FIG. 3, and is perceived by an observer looking at the outer prism 4 in the direction of the arrows X through the transparent part of the needle hub or of the viewing window and of the hollow cavity. The patch is very small and hardly perceptible, as the rays of light are refracted along the arrows X at the bent surfaces of the needle hub 2. This occurs during the transfer of air into the needle hub 2 and then further during the transfer from the needle hub 2 into the hollow cavity 3. The light falling on the outer prism and the light reflected by the outer prism is thus refracted at the boundaries air/needle hub and needle hub/air.

Due to this repeated strong refraction only a small patch having metallic luster appears. The effect of the refraction is described by Snell's law, and for the refraction at the boundary needle hub/air $\sin(\beta)=\sin(\alpha)$ n1/n2 applies, wherein n1 is the refractive index of the needle hub and n2 that of the medium in the hollow cavity 3. The angle α is the incident angle on the boundary needle hub 2/hollow cavity 3, and the angle β is the emergent angle. If air is present in the hollow cavity 3 with n2 ca. 1, then the emergent angle β is larger than when liquor having a refractive index of 1.32 to 1.36 is in the hollow cavity 3. For air in the hollow cavity 3, stronger refraction occurs than for liquor in the hollow cavity 3 at the boundary needle hub/hollow cavity 3. If the refraction of the rays of light is reduced by the presence of liquor in the hollow cavity 3, then the patch with metallic luster, which is only hardly perceptible when air is in the hollow cavity 3, now appears much larger and clearer. This effect can be designed advantageously when the bend at the boundary air/needle hub 2 is very slight, that at the boundary needle hub 2/hollow cavity 3 is very large and the refractive index of the needle hub n1 is very close to that of the liquor. Advantageously, an outer prism as shown in FIG. 7 is made from the same plastic material as the needle hub. Such an arrangement can be manufactured in a production process such as plastic injection moulding without further processing steps.

Instead of an outer prism 4" in the shape of a triple prism or roof prism, a reflective layer 10 can also be applied. As for conventional mirrors, such a layer can consist of a thin layer of aluminium, silver, a sequence of layers having high and low refraction, or the like. This thin layer should correspond in its area to that of the basal plane of the described triple prisms and roof prisms. The function of the reflective layer is the same as in the case of an outer prism. The incident ray of light is reflected by means of the two devices. Here, for the case of use it is not decisive for recognising liquor that in a prism the reflecting ray of light experiences an offset to the incident ray of light and for a reflective layer it does not. Regarding refraction of rays of light and reflection thereof when air or liquor is in the hollow cavity 3, the same optical effects apply for a reflective layer as for an outer prism. Instead of the reflective layer or the outer prism, a reflection grating having reflection characteristics can also be used.

FIGS. 6 and 8 show further advantageous embodiments having an inner prism. Here, by means of the row-wise arrangement of a plurality of prisms on the inner area of the needle hub 2, observation of the liquor backflow from all sides vertically on the spinal cannula is achieved. FIG. 8 shows a particularly advantageous embodiment in which the eye of the user is directed through the recesses 8a in the grip collar 8 functioning as windows and the bend at the boundary air/needle hub 2 in the area of the viewing window is kept very slight, for example by means of a polygonal area in the cross-sectional view.

FIG. 7 shows a further advantageous embodiment having an outer prism. Triple prisms or roof prisms are arranged in two rows which are arranged adjacent each other on the circumference of the transparent needle hub 2. The individual prisms of a row are preferably at a distance from each other such that when viewing along the arrows X, the prism of the same row or of the other row, which prism is arranged on the opposite side, can be seen through this space or through the gap. In a similar way to FIGS. 6 and 8, this arrangement allows the recognition of the liquor backflow from all sides vertical to the longitudinal axis of the spinal cannula.

Figure 3:
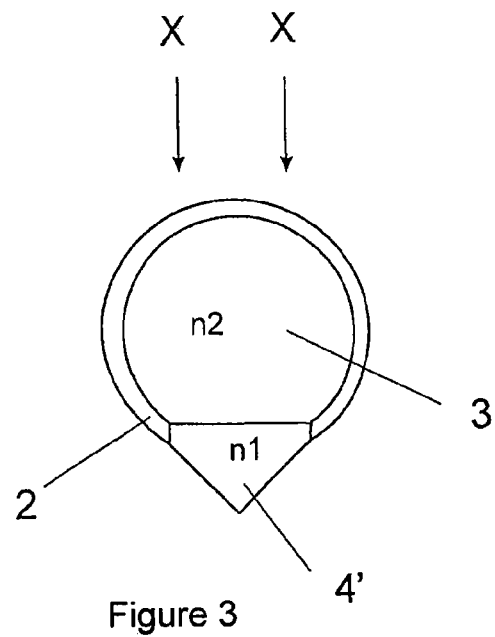

In FIGS. 2 and 3, the prism is inserted in the cross-sectional view of the needle hub in each case such that the basal plane of the prism forms a bevel on the inner circumference or outer circumference of the needle hub. However, it is also possible to mould the prism on the needle hub such that for the inner prism 4 the outer circumference of the needle hub 2 forms a full circle, so that the basal plane of the prism, which in FIG. 2 forms a bevel on the outer circumference, has a bent shape. In the same way, for the outer prism according to FIG. 3, the inner circumference of the hollow cavity 3 can be circular, so that only the side areas of the prism protrude outwards from the otherwise round cross section of the needle hub 2.

Instead of the round cross section of the observation chamber 3 in the needle hub 2 shown, another cross sectional shape can also be provided, especially when the type of light-refracting means is formed differently.

The needle hub 2 can have a circular, elliptical, polygonal or rectangular cross section in the area of the observation chamber 3.

When using an outer prism 4', in the viewing direction X (FIG. 3) a bent area of the hollow cavity 3 and/or of the outer circumference of the needle hub 2 is located opposite this outer prism, wherein the bent area forms the means for refracting light. If an inner prism 4 (FIG. 2) is used, then the delimiting area of the hollow cavity 3 opposite the gable-shaped areas of the inner prism can be designed in different ways, for example the hollow cavity 3 can also have a rectangular or square cross section, as FIG. 2a shows.

Figure 2A:
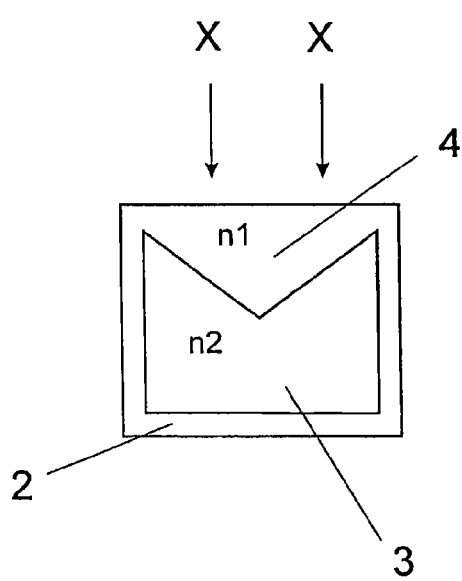

FIG. 2a shows an embodiment of an inner prism 4 for a possible cross section of the hollow cavity or observation chamber 3, which is formed square on the outer circumference and polygonal on the inner circumference.

Figure 2B:
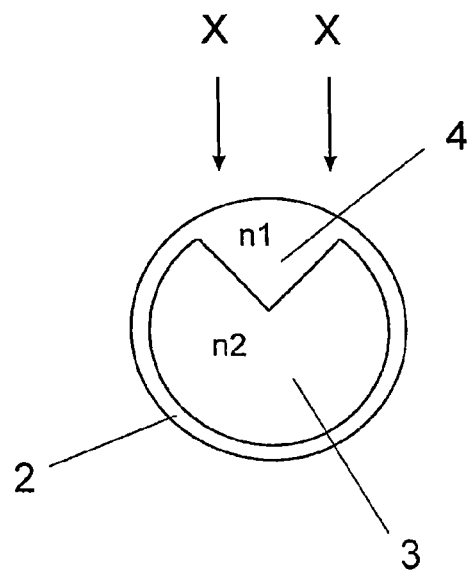

FIG. 2b shows an embodiment of a cross section of a flexible-tube-shaped observation chamber 3 having an inner prism 4.

Figure 3A:
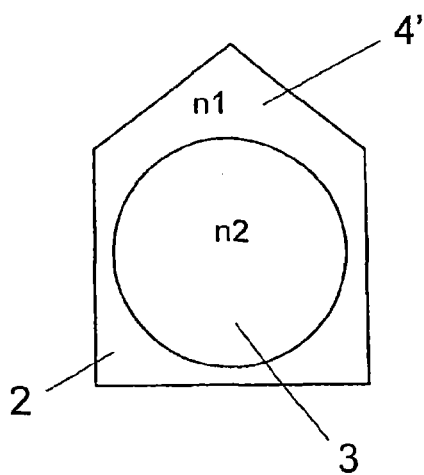

FIG. 3a shows a possible embodiment having an outer prism 4', wherein the outer circumference is designed polygonal or rectangular and the inner circumference of the hollow cavity or of the observation chamber 3 is designed round, so that in the viewing direction X of the outer prism 4', this is associated with at least one bent area.

Figure 3B:
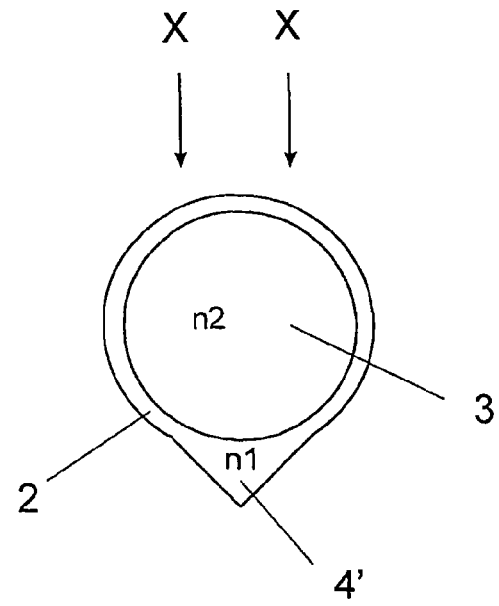

FIG. 3b shows a cross section of a flexible tube having an outer prism 4' as a further embodiment.

In the embodiments according to FIGS. 2 and 3, the prism extends in the axial direction of the needle hub 2. However, it is also possible to arrange a prism or a plurality of prisms adjacent each other transverse or diagonally to the axis of the needle hub.

For the embodiments described, the light-refracting or reflecting means is preferably moulded on the needle hub 2. However, it is also possible, especially for the embodiment according to FIG. 3, to mount the prism 4' as a separate component at the needle hub 2, for example by bonding.

The whole needle hub 2 preferably consists of transparent plastic material.

The reflective layer 10 an also be applied on the convexly bent outer circumference of the needle hub 2, wherein the reflecting side faces the hollow cavity or the observation chamber.

With the described arrangement of inner prism and outer prism, it is not only possible to determine the liquor backflow in a spinal cannula hub, but also generally to determine the presence or absence of transparent fluids in a hollow cavity 3, for example, in aspiration syringes of a different type or in a flexible tube. Possible applications for a flexible tube are, for example, likewise fluid recognition in IV delivery systems or the recognition of air bubbles therein.

Figure 6A:
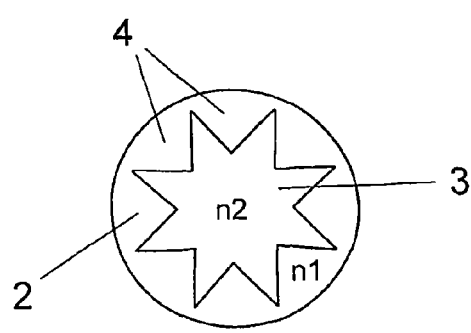

FIG. 6a shows a cross section through the observation chamber in FIG. 6 having inner prisms 4 arranged on the inner circumference.

Figure 7A:
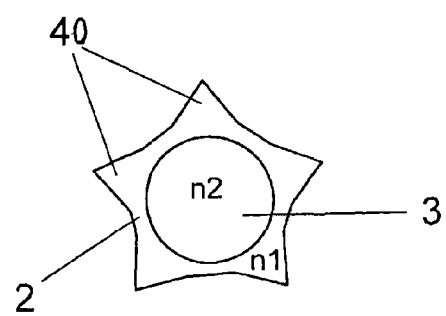

FIG. 7a shows a cross section through the needle hub of FIG. 7 along a row of outer prisms 40. The outer prisms 40 of the adjacent row of prisms are preferably offset in the circumferential direction such that in the view of FIG. 7a the outer prisms 40 are arranged between those of the prisms shown in FIG. 7a.

The invention claimed is:

1. A spinal cannula comprising:
a needle hub having a transparent area for observing liquor flowing through a hollow cavity of the needle hub; and
a prism positioned in or at the transparent area of the needle hub, wherein the prism is configured to refract or reflect rays of light directed towards the needle hub, thereby presenting a metallic luster image responsive to an absence of the liquor in the hollow cavity of the needle hub and a transparent image responsive to a presence of the liquor in the hollow cavity of the needle hub.

2. The spinal cannula according to claim 1, wherein the prism is mounted on the outer circumference of the needle hub or of the transparent area.

3. The spinal cannula according to claim 2, wherein the outer prism, seen in the viewing direction, is associated with at least one bent area of the hollow cavity or of the outer circumference of the needle hub as a means for refracting rays of light.

4. The spinal cannula according to claim 1, wherein at least one prism area delimits the hollow cavity or the observation chamber in the needle hub.

5. The spinal cannula according to claim 1, wherein the prism is moulded on to the spinal cannula.

6. The spinal cannula according to claim 1, wherein the needle hub is surrounded by a grip collar having at least one recess on the circumference which is arranged over the prism.

7. A spinal cannula comprising:
a needle hub having a transparent area for observing liquor flowing through a hollow cavity of the needle hub;
a prism for refracting or reflecting rays of light provided in or at the transparent area of the needle hub, wherein the prism is mounted on the outer circumference of the needle hub or of the transparent area and rows of outer prisms are formed along the circumference offset to each other in the axial direction, and the prisms in each row are at a distance from each other in the circumferential direction.

8. A spinal cannula comprising:
a needle hub having a transparent area for observing liquor flowing through a hollow cavity of the needle hub;
a prism for refracting or reflecting rays of light provided in or at the transparent area of the needle hub, wherein the prism is formed on the inner circumference of an observation chamber in the needle hub.

9. The spinal cannula according to claim 8, wherein a plurality of inner prisms are formed adjacent each other on the inner circumference of the observation chamber in the needle hub.

10. A hollow body including a needle hub having a hollow cavity and at least one transparent wall portion, wherein a prism for refracting or reflecting rays of light is provided in the area of the transparent wall area, the prism configured to present a metallic luster image responsive to an absence of liquor in the hollow cavity of the needle hub and a transparent image responsive to a presence of the liquor in the hollow cavity of the needle hub.

11. The hollow body according to claim 10 wherein the hollow body is a flexible tube.

12. A spinal cannula comprising:
a needle hub having a transparent area for observing liquor flowing through a hollow cavity of the needle hub; and
at least one prism positioned in or at the transparent area of the needle hub, the prism configured to refract or reflect rays of light directed towards the needle hub, thereby presenting a metallic luster image responsive to an absence of the liquor in the hollow cavity of the needle hub and a transparent image responsive to a presence of the liquor in the hollow cavity of the needle hub.

* * * * *

UNITED STATES PATENT AND TRADEMARK OFFICE
CERTIFICATE OF CORRECTION

PATENT NO. : 8,551,059 B2  Page 1 of 1
APPLICATION NO. : 12/936570
DATED : October 8, 2013
INVENTOR(S) : Katerkamp et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 193 days.

Signed and Sealed this

Fifteenth Day of September, 2015

Michelle K. Lee
*Director of the United States Patent and Trademark Office*